United States Patent [19]

Zehner

[11] 4,065,490

[45] * Dec. 27, 1977

[54] PROCESS FOR THE PREPARATION OF OXALATE ESTERS FROM CARBON MONOXIDE AND AN ENOL ETHER

[75] Inventor: Lee R. Zehner, Media, Pa.

[73] Assignee: Atlantic Richfield Company, Los Angeles, Calif.

[ * ] Notice: The term of this patent subsequent to Jan. 17, 1995, has been disclaimed.

[21] Appl. No.: 669,376

[22] Filed: Mar. 22, 1976

[51] Int. Cl.$^2$ .............................................. C07C 69/36
[52] U.S. Cl. ................................. 560/204; 260/465.4; 560/193; 560/196; 560/197; 560/198
[58] Field of Search ............ 260/485 R, 485 L, 485 J, 260/485 P, 485 F, 465.4

[56] References Cited

U.S. PATENT DOCUMENTS 3,393,136  7/1968  Fenton et al. ................... 260/485 R

FOREIGN PATENT DOCUMENTS 2,213,435  10/1973  Germany .............................. 260/485
2,514,685  10/1975  Germany .............................. 260/485

OTHER PUBLICATIONS

Fenton et al., J. Org. Chem. 39, No. 5, 701-704, (1974).

Primary Examiner—Jane S. Myers
Attorney, Agent, or Firm—Delbert E. McCaslin

[57] ABSTRACT

A process for the preparation of oxalate esters by the catalytic oxidative carbonylation of an enol ether with carbon monoxide, an alcohol and oxygen-containing gas in the presence of a metal salt catalyst and an amine base. In addition, a catalytic amount of particular metal oxidizing salts is employed along with a catalytic amount of an acid or an amine salt compound. Alternatively various counterions and ligands of the metal salt catalysts may be employed.

23 Claims, No Drawings

PROCESS FOR THE PREPARATION OF OXALATE ESTERS FROM CARBON MONOXIDE AND AN ENOL ETHER

BACKGROUND OF THE INVENTION

A number of prior art processes have been proposed for the preparation of oxalate esters by the oxidative carbonylation of alcohols in the presence of metal salt catalysts, dehydrating agents and ferric or cupric redox agents in solution.

The present invention is directed to a process for the preparation of oxalate esters in high yield and avoiding the problems associated with the prior art processes of carbonylating alcohols directly to obtain the desired oxalate ester. More particularly, the present process relates to the synthesis of oxalates by reacting carbon monoxide, a particular amount of an alcohol, and oxygen with an enol ether under elevated temperature and pressure conditions in the presence of a catalytic amount of a palladium, platinum, cadmium, cobalt, rhodium, zinc or copper salt catalyst and at least a catalytic amount of an amine base and includes the employment of catalytic amounts of copper (II) or iron (III) oxidant salts in addition to catalytic amounts of an ammonium or substituted ammonium salt compound and ligands of the metal salt catalysts.

U.S. Pat. No. b 3,393,136 describes a process for the preparation of oxalates by contacting carbon monoxide at superatmosheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to prevent the accumulation of water.

In a recent article by Donald M. Fenton and Paul J. Steinwand, Journal or Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g. coppper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Uner non-explosive conditions only trace amounts of oxalate can be obtained.

A more recent West German Patent No. 2,514,685 describes a process for the production of dialkyl oxalates by reacting an aliphatic alcohol with CO and oxygen under pressure in the presence of a catalyst of a mixture of a salt of a metal from the platinum group and a salt of copper or iron and an accelerator including nitrates, sulfates, carbonates, tertiary amines and hydroxides and carboxylates of alkali metals and alkaline earth metals. Conversion of the alcohol employed to the dialkyl oxalates in such process is low.

Many important commercial applications have been developed for the oxalate products of this invention, for example, as cellulose ether or ester and resin solvents, as dye intermediates and the preparation of pharmaceuticals.

The process of the present invention provides a method of carrying out the oxidative carbonylation of enol ethers to produce an oxalate ester without the coproduction of water which acts to poison the catalyst system and which even in small amounts also causes the production of large quantities of carbon dioxide and an attendant loss of the desired oxalate ester. Thus, by the process of the present invention, only very small concentrations of water can accumulate in the reaction system since by the mechanism of the reaction any water which might be formed is rapidly consumed upon formation of a coproduct ketone or aldehyde. In addition, the coproduction of carbonate esters associated with such carbonylation reactions is minimized giving excellent selectivities to oxalate esters with high conversions of the enol ether. The ketone or aldehyde coproduced with the desired oxalate ester by the oxidative carbonylation reaction of the enol ether may be readily separated from the desired oxalate and converted back to the respective reactant enol ether.

Other advantages of the present invention, as compared to known prior art processes for the production of oxalates are (1) elimination of hazardous operational conditions by avoiding exposive mixtures of oxygen and carbon monoxide, (2) avoiding the use of large amounts of corrosive chloride ions (3) ease of recovery and regeneration of the metal salt catalysts for reuse in the process and (4) the ability to employ in the process as catalysts the more readily available copper salts and other metal salts in place of the more expensive platinum group metal salts.

SUMMARY OF THE INVENTION

According to the present invention there is provided a much improved catalytic oxidative carbonylation process for the preparation in high yield of oxalate esters by reacting stoichiometric quantitites of an alcohol, carbon monoxide and oxygen with an enol ether, which process is carried out at elevated temperatures and pressures in the presence of a metal salt catalyst and a catalytic amount of an amine base and under relatively anhydrous conditions. In the process at least one mole of alcohol per mole of enol ether is employed. The process of the invention also utilizes, in appropriate catalytic amounts, particular metal oxidant salts and an acid or an ammonium or substituted ammonium salt compound to provide a pronounced effect on oxalate ester selectivity, and high conversions to the oxalates over the carbonates which may be present in only trace amounts. In addition, it has been found that alternatively catalytic amounts of various ligands, which will not work in themselves, may be used as co-catalysts in conjunction with the metal salt catalysts, the amines, the amine salts and the oxidant salts.

It is a primary object of this invention to provide a process for the preparation of oxalate esters in high yield and high conversion of reactants while avoiding operational problems associated with prior processes.

It is another object of this invention to provide a novel reaction system useful in the conversion of carbon monoxide, oxygen, alcohol and enol ethers to oxalate esters.

It is a further object of this invention to provide a specific mechanism for the employment of catalysts, oxidant salts, amine salts and amines in an oxidative carbonylation process employing enol ethers as reactants.

These and other objects and advantages of this invention will become apparent from the description of the invention which follows and from the claims.

DESCRIPTION OF THE INVENTION

In accordance with the invention, an oxalate ester is produced by reacting, under relatively anhydrous liquid phase conditions, an enol ether with carbon monoxide, at least equal molar quantities of an alcohol based on the enol ether employed and oxygen at elevated temperatures and pressures in the presence of a catalyst comprising palladium, rhodium, platinum, copper, cobalt, cadminum or zinc metal salts, with or without a ligand such as lithium iodide as a co-catalyst, and in catalytic amounts, ammonia or a primary, secondary or tertiary amine and in addition catalytic amount of a copper (II) or iron (III) metal oxidant salt, an ammonium salt or amine salt or acid stronger than water which will not complex too strongly with the metal salt catalyst. The synthesis of the oxalate esters is carried out according to the following postulated equation:

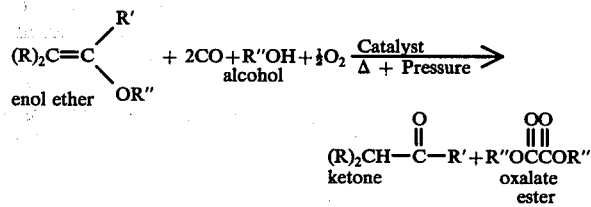

wherein R and R' is hydrogen, an alkyl, alicyclic, aralkyl or aryl group and R" is substituted or unsubstituted alkyl or aralkyl group. R and R' may be the same or different. R and R', except when hydrogen, and R" may also contain such substituents such as amido, alkoxy, amino, carboxy, cyano, fluoro etc. radicals. The substituents, in general, do not interfere with the reaction of the invention. The R" of alcohol shows reaction position.

As indicated above, catalytic amounts of an amine are added to the reacion mixture and as noted, in addition, in catalytic amounts, a metal oxidant salt and an amine salt. The amine salt so added may be formed in situ in the reaction mixture by the addition of an acid such as sulfuric acid in order to form the necessary quantity of amine salt. Thus, for example, triethylamine can be employed initially in sufficient amounts and sulfuric acid added to form triethylammonium sulfate in the desired catalytic quantities. The addition of the amine salt maintains the proton acidity of the reaction system thereby providing an increased selectivity and yield of oxalate ester.

The reaction between the enol ether, carbon monoxide, alcohol and oxygen may be carried out in an autoclave or any other high pressure reactor. A general procedure is to charge the enol ether, amine, alcohol, amine salt (or the required amount of amine and acid), catalyst, and the oxidant salt into the reaction vessel, introduce the proper amount of carbon monoxide and oxygen to the desired reaction pressure and then heat the mixture to the desired temperature for the appropriate period. The reaction can be carried out batchwise or as a continuous process and the order of addition of the reactants may be varied to suit the particular apparatus employed. The reaction products are recovered and treated by any conventional method such as distillation and/or filtration, etc. to effect separation of the oxalate from unreacted materials, catalyst, oxidant salt, amine salt, by products, etc.

The enol ethers employed in stoichiometric quantities and suitable for use in the process of the present invention conform to the general formula

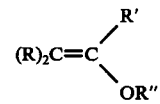

as indicated hereinabove. R and R' may be hydrogen or an alkyl group containing from 1 to 20 carbon atoms preferably 1 to 10 carbon atoms. R and R' may also be an alicyclic, aralkyl or an aryl group containing one or more benzenoid rings preferably not more than 3 rings which may be fused or joined by single valency bonds. R" which may be substituted or unsubstituted alkyl or aralkyl groups preferably contain from 1 to 10 carbon atoms in the alkyl chain and from 1 to 2 aryl group substituents when R" is an aralkyl group.

Representative enol ethers suitable for use in this invention include for example, methyl vinyl ether, ethyl vinyl ether, n-propyl and isopropyl vinyl ether, n-butyl, isobutyl and sec-butyl vinyl ether as well as t-butyl, n-hexyl, n-octyl, 2-ethylhexyl, decyl, cetyl, octadecyl, phenyl and 2,2,2-trifluoroethyl vinyl ether, etc., bis(2-methallyl)vinyl ether, etc., methyl-, ethyl-, propyl-, butyl-1-propenyl ether, etc., 2-buten-2-yl-methyl ether (cis and trans), etc., 2-methyl-2-propen-1-yl methyl ether, etc.

The alcohols employed in at least stoichiometric quantities with the enol ethers and suitable for use in the process of the present invention can be monohydric saturated aliphatic and alicyclic alcohols or aromatic alcohols and may contain other substituents such as amido, alkoxy, amino, carboxy, cyano, etc. radicals in addition to the hydroxyl group. The substituents, in general, do not interfere with the reaction of the invention.

The alcohols which are employed in at least molar quantities equal to the molar quantities of enol ether employed may be primary, secondary or tertiary alcohols and conform to the general formula ROH, wherein R is an optionally substituted aliphatic or alicyclic group preferably containing from 1 to 20 carbon atoms. R may also be an aromatic group containing one or more benzenoid rings preferably not more than 3 rings which may be fused or joined by single valency bonds, directly or through bridging groups which may be, for example, oxygen or sulfur atoms or sulfoxide sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, hexyl, octyl, lauryl, n- and isopropyl, cetyl, benzyl, chlorobenzyl and methoxy-benzyl alcohols as well as, for example cyclohexanol, octanols, heptanols, decanols, undecanols, 2-ethyl hexanol, nonanol, myristyl alcohol, stearyl alcohol, methyl cyclohexanol, pentadecanol, oleyl and eicosonyl alcohols, and the like. The preferred alcohols are the primary and secondary monohydric alcohols, such as methanol, ethanol and n-butyl alcohol.

The amines employed in catalytic quantities in the process of the invention in addition to ammonia may be primary, secondary, or tertiary amines and include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc. The amines may be employed in the reaction in concentrations of from 0.1 to 5 weight percent and preferably at a concentration ∼ 3 weight percent.

Representative amines as hereinabove described, include for example, mono-, di- and tri-methyl, ethyl, and propyl amines, iso- and diisopropylamines, allyl amines, mono-, di-, tri-, iso and diisobutyl amines, 1-methylpropyl amine, 1,1-dimethylethyl amine, amyl amines, cyclohexyl amine, dicyclohexylamine, 1,3-dimethyl-butyl amine, 2-ethylhexylamine, 1-cyclopentyl-2-amino propane, 1,1,3-tetramethylbutylamine, aniline, ethylene diamine, methylene diamines, ethanolamine, octylamines, n-decyl amine, do-, tetra-, hexa-, octa-, dido-, ditetra-, diocta, trido- and triocta-decylamines, chloroanilines, nitroanilines, toluidines, naphthylamine, N-methyl and N-ethyl, and N,N-dimethyl and N,N-diethyl aniline, di- and triphenylamines, N,N-diamylaniline, benzyl dimethyl amine, piperidine, pyrrolidine, etc. The preferred amines are the tertiary amines such as triethylamine and tributyl amine.

The metal salt catalysts which may be employed in the process of this invention are the palladium, platinum, rhodium, copper, cobalt, cadmium and zinc salts. Among the chemical forms of the metal compounds which can be used as such or as mixtures are the palladium, platinum and rhodium, halides, sulfates, oxalates and acetates and the copper halides preferably the palladium (II) and copper (I) or (II) halides such as palladium (II) chloride, palladium (II) iodide, copper (II) chloride and copper (I) iodide. Representative catalytic metal salt compounds include, for example palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, cobalt (II) chloride, cadminum chloride, zinc chloride, etc.

The catalysts employed may be in a homogeneous state in the reaction mixture at reaction conditions. Thus, the catalysts may be present in solution, or suspension and may also be on support materials such as alumina, silica gel, aluminosilicates, activated carbon or zeolites.

The reaction is generally carried out in the presence of a catalytic proportion of the metal salt catalyst and will proceed with small amounts of the metal salt catalyst compounds hereinabove described. Generally the proportions of the metal salt catalyst used in the reaction will be equivalent to between about 0.001 to 5 weight percent of the enol ether employed and are preferably employed in amounts between about 0.01 to 2 percent by weight of the enol ether employed. Larger or smaller amounts may be employed at varied pressures and temperatures.

As mentioned hereinabove, a ligand or coordination complex compound of the metal catalyst may be employed in the process of the invention as a co-catalyst and thereby also achieve a pronounced increase in the selectivity for the oxalate ester. The ligands may be, for example, alkyl or aryl phosphines, arsines, iodides or stibines. The complexes of the metal catalysts which are suitable as co-catalysts in the process of the present invention include complex compounds of palladium, platinum, rhodium, cadminum cobalt, zinc and copper. The complex compounds may contain one or more atoms of the said metals in the molecule and when more than one such atom is present, the metals may be the same or different. The mono- or poly-dentate ligands which are present in the molecule of the complex compounds and in which at least one of the electron-donating atoms is an atom of phosphorous, arsenic or antimony or an iodide ion containing a lone pair of electrons may be, for example, organo-phosphines, -iodides, arsines and -stibines. Suitable mono-dentate ligands include alkyl phosphines such as trimethyphosphine and tributylphosphine, aryl-phosphines such as diethylphenyl-phosphine and radicals derived from such phosphines, for example the radical having the formula —P(CH$_3$)$_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is also preferred to employ alkali metal iodides, e.g. lithium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and SnCl$_3$— groups; molecules which may be bonded to the metal include, for example, organic isocyanides and isothiocyanates.

Examples of suitable complex compounds are those represented by the following formulae:

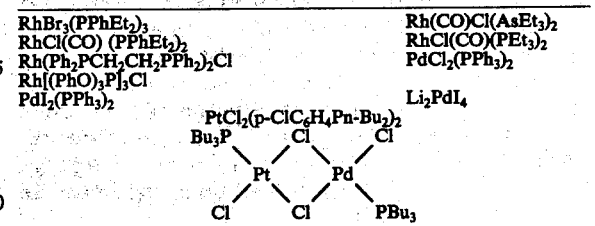

The complex compounds employed may be introduced into the reaction mixture as such, or they may be formed in situ from a suitable metal compound noted above and the desired ligand.

The ligand or complex compounds may be used in catalytic amounts of from 0 to 3 percent preferably from 0.1 to 1 percent by weight of the enol ether to be reacted although larger or smaller amounts may be employed at varied pressures or reaction rates.

The oxidizing salts which may be employed in an anhydrous condition and in catalytic amounts of from 0.1 to 10 weight percent preferably 2 to 5 weight percent in the process of the invention include the copper (II) salts such as the sulfates, trifluoroacetates, oxalates, or acetates preferably the copper (II) sulfates and trifluoroacetates. Representative oxidant salts include, for example, copper (II) sulfate, copper (II) trifluoroacetate, copper (II) acetate, copper (II) oxalate copper (II) triflate and copper (II) fluorosulfonate. Excess chlorides in the form of oxidant salts are detrimental to the reaction system of the present invention. Iron (III) salts such as iron (III) sulfate may also be used in similar proportions in the instant process; the copper salts being preferred.

The amine salts which are employed in an anhydrous condition and in a catalytic amount of from 0.5 to 10 weight percent preferably in a concentration ~ 5 weight percent in the process of the invention include, for example, the ammonium and substituted ammonium sulfates, trifluoroacetates, and acetates, preferably the tertiary amine sulfates such as triethyl ammonium sulfate. Representative amine salts include, for example diethylammonium sulfate, ethylammonium sulfate, butylammonium sulfate, ammonium sulfate, trimethylammonium sulfate, monomethylammonium sulfate, trimethyl ammonium hydrogen sulfate, ammonium acetate, ammonium trifluoroacetate, methyl-, ethyl- and butylammoniumtrifluoroacetate, etc.

The amine salts may be added as such or formed in situ in the required amounts upon the addition of an acid, such as, sulfuric, benzene sulfonic phosphoric, o-boric, p-toluene sulfonic, acetic or trifluoroacetic, to the reaction mixture while using greater than the required quantities of the amine base. The acids which may be used to form the salt include those which do not form a complex with the metal salt catalyst or when employed the metal salt oxidant compounds inactivating the catalyst and oxidant. As indicated hereinabove the acids must be of sufficient strenght, i.e., stronger than water, and such that the anion will not complex with the metal catalyst or oxidant salt. The salts which may be formed in situ may in themselves not necessarily be isolable and may exist in equlibrium in the reaction mixture under carbonylation reaction conditions. Thus, such salts could not be added per se but, as indicated above may be formed in situ upon the addition of a suitable acid to the reaction mixture containing amine.

Although not required, solvents, if desired, which are chemically inert to the components of the reaction system may be employed. Suitable solvents include, for example, organic esters such as ethyl acetate, n-propyl formate, iospropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, acetone, cyclhexanone, methyl formate, etc.

As indicated above the reaction can be suitably performed by introducing the oxygen and carbon monoxide at a desired pressure into contact with the alcohol and enol ether reaction medium containing the specified reactants, catalyst, and amine and in addition an amine salt and oxidant salt and heating to the desired temperature. In general, a carbon monoxide pressure of about 500 psig partial pressure and preferably from 900 psig to about 2200 psig is employed. Stoichiometric quantities of carbon monoxide are generally employed. However, an excess of carbon monoxide may be employed, for example, in continuous processes where large excess of or high carbon monoxide requirements are generally utilized, a suitable recycle of the carbon monoxide may be employed. The reaction will proceed at temperatures of from about 50° C. to 200° C. It is generally preferred to operate the process at temperatures in the range of 100° C. to 135° C. to obtain a convenient rate of reaction. Heating and/or cooling means may be employed interior and/or exterior of the reaction to maintain the temperature within the desired range.

At least stoichiometric amounts of oxygen or an oxygen containing gas such as air are generally employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The reaction time is generally dependent upon the enol ether being reacted, temperature, pressure and on the amount and type of catalyst being charged as well as the type of equipment being employed. Reaction times will vary dependent on whether the process is continuous or batch.

The following examples are provided to illustrate the invention in accordance with the principles of this invention but are not to be construed as limiting the invention in any way except as indicated by the appended claims.

In the Examples which follow the reactions are run in a 500 ml stainless steel stirred autoclave. The liquid and solid materials are charged to the reactor (as solutions whenever possible). CO is charged to the reactor, to the desired pressure which is heated to reaction temperature. A CO flow rate is established and air flow added in such an amount that a potentially explosive gas mixture is never obtained in the reactor. When an exotherm is observed, cold water is circulated through the internal cooling coil to maintain the reaction temperature within $\pm$ 1° C. Gas samples of the effluent are obtained periodically and analyzed for $CO_2$ by mass spectral analysis. The reactor is cooled to ambient temperature. During venting of the reactor, gas samples are obtained, and the composition determined by mass spectral analysis. The liquid product is analyzed by gas-liquid phase chromatography (glc) for the oxalate and carbonate ester

EXAMPLE I

A solution of tributylamine (9.27 g.; 50 mmoles), concentrated $H_2SO_4$ (1.72 g.; 16.9 mmoles), n-butyl alcohol (111.2 g.; 1.50 moles), and butyl vinyl ether (80.13 g.; 0.80 mole) is charged to the autoclave fitted with a condenser (-20° C.) and liquid separator on the downstream side. Palladium (II) sulfate (0.24 g.; 1.0 mmoles) and copper (II) sulfate (5.17 g.; 32.4 mmoles) are charged as solids. Carbon monoxide is charged to the autoclave to 1800 psig and heated to 90° C. with a stirring rate of 1500 rpm. A carbon monoxide flow rate is established at 4.35 l./min. and an air flow of 1.00 l./min. started. An exotherm is noted and a constant temperature is maintained with tap water ($\pm$ 1° C.). Gas samples of the effluent gases are collected periodically during the run and analyzed for $CO_2$ by mass spectral analysis.

The reaction is run for 180 minutes then cooled to ambient temperature with tap water. The gas flows are stopped, and the reactor carefully vented. During venting, gas samples are collected and analyzed for $CO_2$.

The reaction product is vacuum filtered and analyzed by glc analysis showing the presence of dibutyl oxalate and only a trace amount of dibutyl carbonate along with acetaldehyde. Minor amounts of 1,1-dibutoxyethane, unreacted butyl alcohol and butyl vinyl ether are also detected in the reaction product. The filtered product contains copper (II) oxalate hemihydrate.

EXAMPLE II

The procedure and operating conditions of Example I are repeated employed the following materials: 5.06 g. (50 mmoles) of triethylamine, 1.72 g. (16.9 mmoles) of concentrated sulfuric acid (96.4 percent), 69.1 g. (1.50 moles) of ethanol, 57.7 g. (0.80 mole) of ethyl vinyl ether, 0.24 g. (1.0 moles) of palladium (II) sulfate and 5.17 g. (32.4 mmoles) of copper (II) sulfate. Gas-liquid phase chromatographic (glc) analysis of the filtered reaction product shows the presence of diethyl oxalate, acetaldehyde, and a trace amount of diethyl carbonate along with small amounts of acetal, unreacted ethyl alcohol and ethyl vinyl ether. Copper (II) oxalate hemihydrate is present.

EXAMPLE III

The procedure of Example I is repeated. A mixture of 5.06 g. (50 mmoles) triethylamine, 1.93 g. (17 mmoles) trifluoroacetic acid, 76.9 g. (2.4 moles) methanol, 57.7 g. (0.80 mole) methylpropen-2-yl ether, 0.21 g. (1.0 mmole) rhodium (III) chloride, 9.4 g. (32.4 mmoles) copper (II) trifluoroacetate is charged the autoclave. The CO is charged to the autoclave to 1700 psig. The temperature is raised to 100° C. with stirring. CO flow rate of 4.35 l./min. and an air flow rate of 1.38 l./min. are established. The temperature is maintained (± 1° C.) and the reaction run for 180 minutes. Dimethyl oxalate, acetone, and a trace amount of dimethyl carbonate and 2,2-dimethoxypropane along with a minor amount of unreacted methanol is detected in the reaction product by glc analysis. The filtered solid contains a minor amount of copper (II) oxalate hemihydrate.

EXAMPLE IV

The procudure of Example I is reapeated. A mixture of 9.27 g. (50 mmoles) tributylamine, 1.72 g. (16.9 mmoles) concentrated sulfuric acid, 76.9 g. (2.4 moles) methanol, 57.7 g. (0.80 mole) methylpropen-2-yl ether, 0.22 g. (1.0 mmole) palladium (II) acetate, 1.05 g. (4.0 mmoles) triphenylphosphine, and 5.17 g. (32.4 mmoles) of copper (II) sulfate is charged to the autoclave. The CO is charged to 1800 psig. The temperature is raised to 50° C. with stirring. A CO flow rate of 4.35 l./min. and an air flow rate of 1.00 l./min. are established. The temperature is maintained (± 1° C.) and the reaction run for 180 minutes. Dimethyloxalate (0.88 mole), acetone, and a trace amount of dimethyl carbonate along with unreacted methanol as well as some 2,2-dimethoxypropane is detected in the reaction product by glc analysis. Copper (II) oxalate hemihydrate is contained in the reaction product.

EXAMPLE V

The procedure of Example I is repeated. A mixture of 5.06 g. (50 mmoles) triethylamine, 1.72 g. (16.9 mmoles) concentrated sulfuric acid, 36.8 g. (0.80 mole) ethyl alcohol, 68.9 g. (0.80 mole) ethyl propen-2yl ether, 0.64 g. (2.0 mmoles) zinc iodide, 0.27 g. (2.0 mmoles) lithium iodide and 5.17 g. (32.4 mmoles) copper (II) sulfate is charged to the autoclave. CO is charged to the autoclave to a pressure of 1800 psig. The temperature is raised to 125° C. with stirring and a CO flow rate of 4.35 l./min. and an air flow rate of 1.38 l./min. are established. The temperature is maintained and the reaction run for 160 minutes. Diethyloxalate, acetone, a trace amount of diethyl carbonate along with unreacted ethyl alcohol and a trace of 2,2-diethoxypropane and some copper (II) oxalate hemihydrate is detected in the reaction product.

I claim:

1. An process for the preparation of oxalate esters which comprises reacting under substantially anhydrous conditions an enol ether having the formula

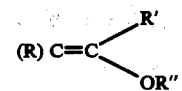

wherein R and R' may be hydrogen, an alkyl, alicyclic, aralkyl or aryl group, and R" is an alkyl or aralkyl group, which R and R', except when hydrogen, and R" may contain other substitutents which do not interfere with the reaction, with carbon monoxide, a monohydric alcohol, having the formula R"OH wherein R" is defined above and oxygen, at a pressure of between about 500 psig and 3000 psig and at a temperature in the range of about 50° C. to 200° C. in the presence of an effective amount of a catalyst selected from the group consisting of palladium, platinum, rhodium, cadmium, cobalt, zinc and copper salt compounds or mixtures thereof, and a catalytic amount of
   a. an aliphatic, cycloaliphatic, aromatic or heterocyclic amine or ammonia,
   b. a copper (II) or iron (III) oxidant salt compound, and
   c. an ammonium or substituted ammonium salt compound, and recovering the desired oxalate ester.

2. A process according to claim 1 wherein the catalyst salt compound is selected from the group consisting of palladium, platinum, rhodium, cadmium, cobalt and zinc halides, oxalates, sulfates and acetates and copper halides.

3. A process according to claim 2 wherein the catalyst is selected from palladium sulfate, palladium chloride, palladium iodide, palladium acetate, copper iodide, cobalt chloride, cadminum chloride, rhodium chloride and zinc chloride.

4. A procss according claim 3 wherein the catalyst is palladium iodide or palladium sulfate.

5. A process according to claim 3 wherein the catalyst is copper iodide.

6. A process according to claim 1 wherein the amine is employed in concentration of from 0.1 to 5 weight percent.

7. A process according to claim 6 wherein the amine is triethylamine.

8. A process according to claim 1 wherein the enol ether is selected from the group consisting of ethyl vinyl ether, n-butyl vinyl ether, methyl propen-2-yl ether, and ethyl propen-2yl ether.

9. A process according to claim 1 wherein the alcohol is selected from the group consisting of methyl alcohol, ethyl alcohol and n-butyl alcohol.

10. A process according to claim 9 wherein the alcohol is methyl alcohol.

11. A process according to claim 1 wherein the oxidant salt compound is copper (II) or iron (III) oxalate, sulfate, acetate or trifluoroacetate.

12. A process according to claim 11 wherein the oxidant salt is copper (II) sulfate.

13. A process according to claim 11 wherein the oxidant salt is iron (III) sulfate.

14. A process according to claim 1 wherein the ammonium salt compound is triethylammonium sulfate.

15. A process according to claim 1 wherein the ammonium or substituted ammonium salt compound is formed in situ upon the addition of an acid to the reaction mixture containing an excess of amine over the required quantities of amine base for the reaction, said acid being of a strength stronger than water and such that the anion will not complex with the metal salt catalyst or metal oxidant salt compound.

16. A process according to claim 15 wherein said acid is sulfuric acid.

17. A process according to claim 15 wherein said acid is trifluoroacetic acid.

18. A process according to claim 1 wherein the reaction is carried out in the presence of a cocatalytic amount of an organic mono- or poly-dentate ligand or co-ordination complex of the metal catalyst selected from the group consisting of alkyl, aryl and halogen substituted phosphines, arsines, stibines and iodides.

19. A process according to claim 18 wherein the ligand or co-ordination complex is triphenylphosphine.

20. A process according to claim 18 wherein the ligand or co-ordination complex is lithium iodide.

21. A process according to claim 1 wherein the pressure is between about 900 psi and 2200 psi and the temperature is in the range of about 100° C. to 135° C.

22. A process according to claim 1 wherein air is employed as a source of oxygen for the reaction.

23. A process according to claim 1 wherein the catalyst is supported.